United States Patent [19]

Schlüter et al.

[11] Patent Number: 4,659,736

[45] Date of Patent: Apr. 21, 1987

[54] BENZOYL UREA COMPOUNDS AS AGENTS FOR REPELLING SNAILS AND SLUGS

[75] Inventors: Klemens Schlüter, Singapore, Singapore; Hans-Jürgen Schnorbach, Leverkusen, Fed. Rep. of Germany

[73] Assignee: Bayer Aktiengesellschaft, Leverkusen, Fed. Rep. of Germany

[21] Appl. No.: 691,089

[22] Filed: Jan. 11, 1985

[30] Foreign Application Priority Data

Jan. 21, 1984 [DE] Fed. Rep. of Germany ....... 3402074

[51] Int. Cl.⁴ ..................... A01N 37/02; A01N 37/10; A01N 43/32; A01N 47/28
[52] U.S. Cl. ........................... 514/452; 424/DIG. 10; 514/150; 514/256; 514/258; 514/269; 514/272; 514/274; 514/302; 514/344; 514/345; 514/348; 514/349; 514/351; 514/353; 514/375; 514/376; 514/377; 514/521; 514/522; 514/584; 514/594; 514/919
[58] Field of Search ............... 424/DIG. 10; 514/522, 514/584, 594, 919, 150, 256, 258, 269, 272, 274, 302, 344, 345, 348, 349, 351, 353, 375, 377, 376, 521, 452

[56] References Cited

U.S. PATENT DOCUMENTS 4,277,499 7/1981 Sirrenberg et al. .................. 514/594
4,468,405 8/1984 Rigterink et al. .................... 514/594
4,508,734 4/1985 Lange et al. ......................... 514/594

Primary Examiner—Allen J. Robinson
Attorney, Agent, or Firm—Sprung Horn Kramer & Woods

[57] ABSTRACT

A method of combating slugs and snails comprising applying to a plant or to an area from which it is desired to exclude such slugs and snails a repellent amount of at least one benzoyl urea of the formula

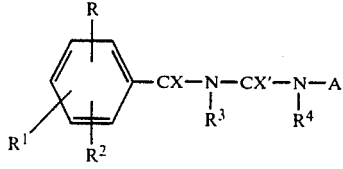

in which
R, $R^1$ and $R^2$ each independently is hydrogen, alkyl, alkoxy or halogen,
$R^3$ and $R^4$ each independently is hydrogen, alkyl, aralkyl, aryl, alkoxy, aralkoxy, aryloxy, alkylthio, aralkylthio or arylthio,
A is an aromatic or heteroaromatic radical, and
X and $X^1$ each independently is oxygen or sulphur.

6 Claims, No Drawings

BENZOYL UREA COMPOUNDS AS AGENTS FOR REPELLING SNAILS AND SLUGS

The present invention relates to the novel use of certain benzoyl ureas for protecting plants from damage by snails and slugs.

It is known that board destruction of all terrestrial snails and slugs is possible, especially by means of baits and sprays based on methaldehyde and mercaptodimethur. A large number of other active compounds customarily used in plant protection have a more or less specific action in the case of individual species. As for the deterrents of bird pests, too, agents which act as a deterrent against infestation and damage are preferred within the framework of integrated combating measures. According to Godan, "Schadschnecken" ("snail and slug pests"), Verlag Ulmer 1979, pages 267, such preparations have been unknown hitherto.

A large number of benzoyl ureas have been disclosed as highly effective compounds for combating arthropods, in particular insects (see, for example, Chemie der Pflanzenschutz- und Schädlingsbekämpfungsmittel (Chemistry of plant protection agents and pest-combating agents), volume 6, Springer Verlag, Berlin-Heidelberg-New York, 1981, pages 423 to 464).

In open air trails, it has surprisingly been found that certain benzoyl ureas, preferably applied as sprays, repel terrestrial slugs and snails and deter them from causing damage, and can thus protect the treated plants from damage.

It has been found that the benzoyl ureas of the general formula

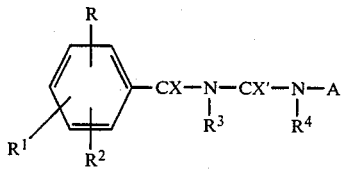

(I)

in which
R, $R^1$ and $R^2$ are identical or different and represent hydrogen, alkyl, alkoxy or halogen,
$R^3$ and $R^4$ are identical or different and represent hydrogen, alkyl, aralkyl, aryl, alkoxy, aralkoxy, aryloxy, alkylthio, aralkylthio or arylthio and
A represents an aromatic or heteroaromatic radical and
X and X' are identical or different and represent oxygen or sulphur, repel terrestrial slugs and snails and deter them from causing damage, and can therefore be used for protecting crop plants and ornamental plants from damage by slugs and snails.

Preferred compounds of the general formula (I) are those in which the stated radicals have the meanings set out below: The alkyl and alkoxy radicals, R, $R^1$ and $R^2$ are straight-chain or branched and each contain preferably 1 to 6, particularly preferably 1 to 4 and very particularly preferably 1 or 2, carbon atoms. Methyl, ethyl, methoxy and ethoxy may be mentioned as examples.

Halogen, R, $R^1$ and $R^2$ denotes fluorine, chlorine, bromine and iodine, preferably fluorine and/or chlorine.

Preferably, at least one of the radicals R, $R^1$ and $R^2$ represents hydrogen and the two other radicals are in the 2,4-, or 2,5-position or particularly preferably in the 2,6-position. If two of the radicals R, $R^1$ and $R^2$ denote hydrogen, the remaining radical is preferably in the 2-position of the phenyl ring.

The alkyl, alkoxy and alkylthio radicals $R^3$ and $R^4$ are straight-chain or branched and preferably contain 1 to 6, in particular 1 to 4 and particularly preferably 1 or 2, carbon atoms. Methyl, ethyl, methoxy, ethoxy, methylthio and ethylthio may be mentioned as examples.

Aryl, aryloxy and arylthio $R^3$ and $R^4$ preferably represent phenyl, phenoxy and phenylthio, and these radicals can be monosubstituted or polysubstituted. 2-Chloro-4-methylphenyl, 4-nitrophenoxy and 4-chlorophenylthio may be mentioned as examples.

In the aralkyl, aralkoxy and aralkylthio radicals $R^3$ and $R^4$, the aryl parts preferably denote phenyl. The alkyl parts contain preferably 1 to 4, in particular 1 or 2, carbon atoms. These radicals can be monosubstituted or polysubstituted, preferably monosubstituted to trisubstituted, in the aryl and/or alkyl part. The following may be mentioned as examples: benzyl, 2-methyl-4-chlorophenylethyl, benzyloxy and benzylthio.

$R^3$ and $R^4$ preferably represent hydrogen.

X and X' preferably represent oxygen.

The aromatic radical A preferably represents a phenyl radical which can be substituted by one or more, preferably 1 to 3, in particular 1 or 2, identical or different radicals.

The heteroaromatic radical A is preferably a 5-membered or 6-membered ring containing one or more, preferably 1 to 3, in particular 1 or 2, identical or different hetero atoms, such as oxygen, sulphur and/or nitrogen, and the heteroaromatic radical A can be one or polysubstituted, preferably monosubstituted to trisubstituted, in particular monosubstituted or disubstituted, by identical or different substituents. Pyridine, primidine, pyrazole, imidazole, triazole, oxazole, thiazole and furazone rings may be listed as examples of heteroaromatic rings. The pyridyl ring may be preferably mentioned, and the pyridyl ring can also be in the from of the N-oxide.

The following may be mentioned as examples of substituents of the aromatic of heteroaromatic radical A: alkyl having preferably 1 to 4, in particular 1 or 2, carbon atoms, such as methyl, ethyl, n- and i-propyl and n-, i- and t-butyl; alkoxy having preferably 1 to 4, in particular 1 or 2, carbon atoms, such as methoxy, ethoxy, n- and i-propoxy and n-, i- and t-butoxy; alkylthio having preferably 1 to 4, in particular 1 or 2, carbon atoms, such as methylthio, ethylthio, n- and i-propylthio and n-, i- and t-butylthio; halogenoalkyl having preferably 1 to 4, in particular 1 or 2, carbon atoms and preferably 1 to 5, in particular 1 to 3, halogen atoms, the halogen atoms being identical or different and preferably being fluorine, chlorine or bromine, in particular fluorine, such as trifluoromethyl; halogenoalkoxy or halogenoalkylthio having preferably 1 to 6, in particular 1 to 4 and particularly preferably 1 or 2, carbon atoms and preferably 1 to 5, in particular 1 to 3, identical or different halogen atoms, such as fluorine, chlorine or bromine, for example trifluoromethoxy, trifluoromethylthio and the radicals $OCHF_2$, $OCF_2$—$CHCl_2$, —$OCF_2$—$CHF_2$, —$OCF_2$—$CHF_2$ and —$OCF_2CHFCF_3$; alkenyl and alkinyl groups having preferably up to 4 carbon atoms, which can be substituted by halogen, such as fluorine and/or chlorine; alkenyloxy and alkinyloxy groups having up to 4 carbon atoms, which can be substituted by halogen; hydroxyl, halogen, preferably fluorine, chlorine, bromine and iodine, in particular chlorine and bromine; cyano; nitro; amino; monoalkyl- and dialkyl-amino having preferably 1 to 4, in particular 1 or 2, carbon atoms per alkyl group, such as methylamino, methyl-ethyl-amino, n- and i-propylamino and methyl-n-butylamino; carboxyl; carbalkoxy having preferably 2 to 4, in particular 2 or 3, carbon atoms, such as carbomethoxy and carboethoxy; sulpho ($-SO_3H$); alkylsulphonyl having preferably 1 to 4, in particular 1 or 2, carbon atoms, such as methylsulphonyl and ethylsulphonyl; arylsulphonyl having preferably 6 or 10 aryl carbon atoms, such as phenylsulphonyl; and the groups $-O-CQ_2-OCQ_2-$, $-OCQ_2-O-$ and $-O-CQ_2-CQ_2-O-$, in which Q represents hydrogen and/or identical or different halogen atoms (preferably fluorine or chlorine), such as $-O-CF_2-O-CF_2-$, $-O-CF_2O-$, $-OCF_2-CF_2O-$ or $-O-CF_2-CFCl-O-$, these groups, together with the atoms of the aromatic or heteroaromatic rings A to which they are bonded, forming 5 or 6-membered rings.

Instead of, or in addition to, the substituents listed above, the aromatic or heteroaromatic radicals A can contain a substituent of the general formula $-Y-B$ in which
Y represents oxygen, sulphur, alkylene having 1 to 4 (preferably 1 or 2) carbon atoms, the $-N=N-$ group or a direct bond and
B represents an aromatic or heteroaromatic radical.

The radical B preferably has the meaning given above for the aromatic or heteroaromatic radical A. The aromatic or heteroaromatic radical B can carry one or more, preferably 1 to 5, in particular 1 to 3, identical or different substituents, the substituents given in the case of radical A being preferred.

Compounds according to the invention, of the general formula (II)

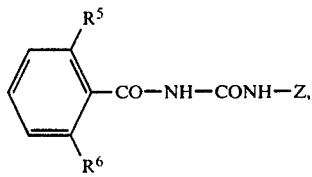

in which
$R^5$ represents hydrogen, methyl, methoxy or halogen (preferably fluorine or chlorine),
$R^6$ represents methyl, methoxy or halogen (preferably fluorine or chlorine) and
Z represents optionally substituted radicals from the series comprising phenyl, pyridyl, pyridyl-N-oxide, oxazolyl, phenoxyphenyl, pyridyloxyphenyl, phenylazobenzene and phenylpyrimidine,
are preferably employed.

Z particularly preferably represents the phenyl radical, the phenoxyphenyl radical or the pyridyloxyphenyl radical, and very particularly preferably represents the phenyl radical.

The substituents in the radicals Z can be one or more, preferably 1 to 4, in particular 1 to 3, identical or different substituents from amongst those stated as substituents for the radicals A and B.

Particularly preferred substituents in the radicals Z are halogen (preferably fluorine and/or chlorine), nitro, cyano, $C_1-C_4$-alkyl which can be substituted by fluorine and/or chlorine (such as $CH_3$ or $CF_3$), $C_1-C_4$-halogenoalkoxy (such as $OCF_3$ or $OCF_2-CHCl_2$), $C_1-C_4$-halogenoalkylthio (such as $SCF_3$) or $-O-CQ_2-CQ_2-O-$, wherein Q is identical or different and represents hydrogen, fluorine or chlorine (such as $-O-CF_2-CF_2-O-$ or $-O-CF_2-CFCl-O-$).

For example, the following compounds can be listed as benzoyl ureas which can be used according to the invention:

| Formula: | Compound No.: |
|---|---|
|  | 1 |

-continued
| Formula: | Compound No.: |
|---|---|
| 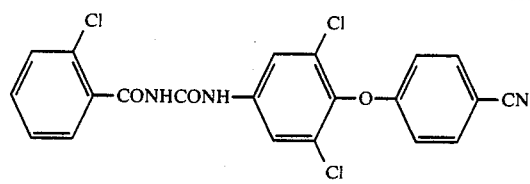 | 4 |
| 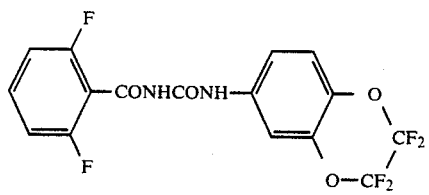 | 5 |
| 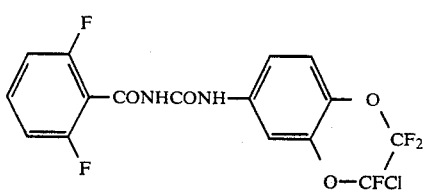 | 6 |
| 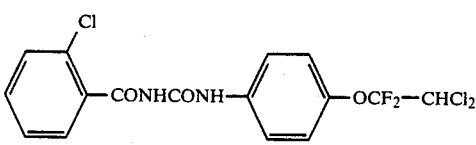 | 7 |
| 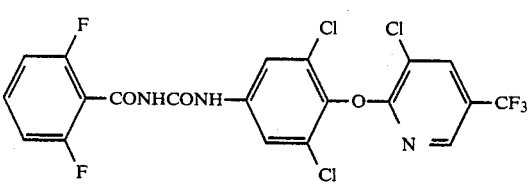 | 8 |
| 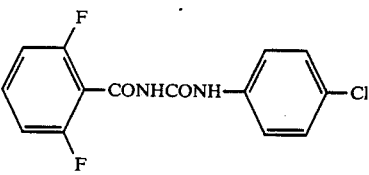 | 9 |
| 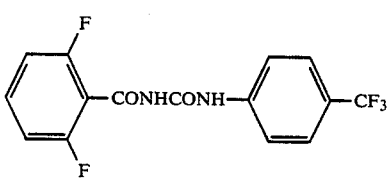 | 10 |
| 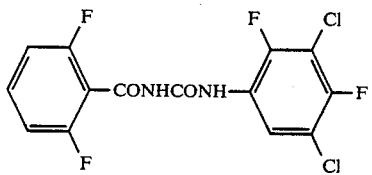 | 11 |

| Formula: | Compound No.: |
|---|---|
| ![structure: 2,6-difluorophenyl-CONHCONH-(2,5-dichloro-4-(OCF2-CHCF2)phenyl)] | 12 |

The benzoyl ureas of the general formula (I) which can be used according to the invention are known (as insecticides) and/or can be obtained by well known methods, see, for example (PS=Patent Specification):
De-A-No. 24 387 47
U.S. Pat. No. 3,992,553
DE-A-No. 2 504 982
DE-A-No. 2 504 984
DE-A-No. 2 504 983 (U.S. Pat. No. 4,041,177)
DE-A-No. 2 528 917
DE-A-No. 2 531 202 (U.S. Pat. No. 4,068,002)
DE-A-No. 2 531 279 (U.S. Pat. No. 4,085,226)
DE-A-No. 2 537 413 (U.S. Pat. No. 4,005,223)
DE-A-No. 2 601 780 (U.S. Pat. No. 4,139,636)
DE-A-No. 2 637 947 (U.S. Pat. No. 4,103,022) p0 DE-A-No. 2 638 233 (U.S. Pat. No. 4,194,005)
DE-A-No. 2 801 316 (U.S. Pat. No. 4,277,499)
DE-A-No. 2 837 086 (U.S. Pat. No. 4,276,310)
U.S. Pat. No. 4,234,600
DE-A-No. 3 023 328
DE-A-No. 2 123 236 (U.S. Pat. No. 3,748,356)
U.S. Pat. No. 4,399,152
U.S. Pat. No. 4,170,657
European Patent PS No. 23,884
DE-A-No. 3 314 383
European Patent Application No. 31,974
U.S. Pat. No. 4,405,552
DE-A-No. 3 033 512 (U.S. Pat. No. 4,310,530)
European Patent Application No. 38,776
U.S. Pat. No. 4,310,694
U.S. Pat. No. 4,310,548
DE-A-No. 3 026 825
European Patent PS No. 13,414 (DE-A-No. 2 901 334 and DE-A-No. 2 927 123)
DE-A-No. 3 003 112
DE-PS No. 3 235 419
European Patent Application No. 55,213
European Patent Application No. 56,124
European Patent Application No. 71,279
European Patent Application No. 30,518
European Patent Application No. 44,278
DE-A-No. 3 044 055
European Patent PS No. 8,880
Japanese Application No. 3,023,871
Japanese Application No. 3,023,872
U.S. Pat. No. 4,380,641
European Patent Application No. 79,311
Japanese Application No. 58 03 51 63
Japanese Application No. 58 03 51 74
U.S. Pat. No. 4,380,641
DE-A-No. 2 928 410
U.S. Pat. No. 4,293,552
DE-A-No. 3 133 009
European Patent Application No. 52,833
DE-A-No. 3 233 383
European Patent Application No. 74,074
DE-A-No. 3 241 138
European Patent Application No. 23,884
Japanese Application No. 58 07 25 66
European Patent Application No. 38,776
European Patent Application No. 88,343
European Patent Application No. 70,130
U.S. Pat. No. 4,405,552
European Patent Application No. 14,674
Japanese Application No. 83 04 09 46
Japanese Application No. 83 04 09 47
U.S. Pat. No. 4,321,276
European Patent Application No. 40,179
European Patent Application No. 35,084
European Patent PS No. 40 30
European Patent Application No. 42,732
European Patent Application No. 44,410
U.S. Pat. No. 4,321,388
U.S. Pat. No. 4,323,579
U.S. Pat. No. 4,321,276
European Patent Application No. 50,321
U.S. Pat. No. 4,323,579
DE-A-No. 3 046 672
DE-A-No 3 141 232
U.S. Pat. No. 4,336,264
DE-A-No. 3 126 263
U.S. Pat. No. 4,344,951
U.S. Pat. No. 4,350,706
U.S. Pat. No. 4,348,412
U.S. Pat. No. 4,353,925
European Patent Application No. 8,768
European Patent Application No. 8,881
European Patent Application No. 65,487
European Patent Application No. 63,413
U.S. Pat. No. 4,348,412
European Patent Application No. 60,071
European Patent Application No. 25,363
U.S. Pat. No. 4,338,321
European Patent Application No. 57,888
DE-A-No. 3 104 407
U.S. Pat. No. 4,366,155
European Patent Application No. 72,438
Japanese Application No. 57 17 51 58
Japanese Application No. 57 16 33 66
Japanese Application No. 82 05 37 86
Japanese Application No. 57 14 42 58
Japanese Application No. 57 12 86 71
Japanese Application No. 57 03 16 64
Japanese Application No. 57 06 46 04
Japanese Application No. 57 18 85 61
DE-A-No. 3 223 505
DE-A-No. 3 217 620
DE-A-No. 3 217 619
DE-A-No. 3 309 987
DE-A-No. 3 311 703

The benzoyl ureas of the general formula (I) have properties which make is possible to use them for combating slugs and snails. Frequently, the repellent action of these compounds, and their deterrent effect against damage, can be detected in laboratory trials only with difficulty and at relatively high doses. In the open air, however, outstanding effects are observed in agricultural and horticultural plant cultures, even for very low application rates. Preferably, sensitive lettuce, vegetable and fruit crops (such as strawberry crops) and cultures of ornamental plants and flowers are protected against damage by slugs and snails.

The action of the benzoyl ureas which can be used according to the invention extends to all terrestrial slugs and snails which occur in large numbers are polyphagous pests in agricultural and horticultural cultures. These include some particularly important pests, such as, for example, the slugs Arion refus (red slug); Arion ater and other Arionidae, Limax species and the field slugs, including Deroceras reticulatum and D. agreste from the Limacidae family, as well as species from the Milacidae family. The snails, including the genera Gattungen Bradybaena, Cepaea, Cochlodina, Discus, Euomphalia, Galba, Helicigona, Helix, Helicella, Helicodiscus, Lymnaea, Opeas, Vallonia and Zonitoides, also cause damage.

The active compounds can be converted to the customary formulations, such as solutions, emulsions, suspensions, powders, foams, pastes, granules, aerosols, natural and synthetic materials impregnated with active compound, very fine capsules in polymeric substances an in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam forming agents. In the case of the use of water as an extender, organic solvents, can, for example also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms.

The active compounds can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms, by applying the active compounds to the plants or to the environment of the plants to be protected, for example, to the soil. The active compounds are preferably applied to the plants to be protected, application by the spray method being very particularly preferred.

Preferably 10 to 1,000 g, in particular 25 to 300 g and very particularly preferably 40 to 150 g of active compound are employed per hectare of cultivated area.

The efficiency of the benzoyl ureas of the general formula (I) which can be used according to the invention can be illustrated by the following Examples (all % ages are % ages by weight): (A) Laboratory trials

EXAMPLE 1

Groups of 5 slugs (Arion rufus) are left in a cage with 4 fresh lettuce leaves for 17 hours, under controlled test conditions. These are single-choice trials in which either leaves which have been treated by means of one spray application or untreated leaves are offered. The active compound concentration in the spray liquor is 0.5%. The extent of damage is determined on the basis of weight differences and photocopies of the damaged picture, and according to visual assessment criteria.

In the case of the leaves treated with, for example, the abovementioned compounds 1 and 6, the damage was greatly reduced compared with the untreated control; the treated leaves were in general not consumed or showed only small traces of damage, whereas the untreated leaves showed very pronounced damage.

EXAMPLE 2

The effect of benzoyl ureas in deterring damage can be demonstrated even under more difficult test conditions, in a multiple-choice trial. Young lettuce plants are treated with the spray liquor (active compound concentration 0.1%) and are planted in test boxes having a soil area of 0.25 m², which are used for snails and slugs. 2 treated lettuce plants and 2 untreated lettuce plants are located diagonally opposite each other in the corners of each test box. Each box contains 5 slugs (Arion rufus). The damage is monitored on 5 successive days.

The lettuce plants which were treated with, for example, the abovementioned compounds 6 and 7 were found to have substantially less damage than the untreated control plants.

B. Open air trials

EXAMPLE 3

Plots which are equal in size and randomly distributed over the trial area are treated repeatedly with the test preparations. 7 days after final treatment, the damage by snails or slugs is rated visually for 24 lettuce plants per plot. The degree of damage is expressed as % damage.

| Active compound Compound No. | Amount applied in kg of active compound/ha | Degree of damage in % |
| --- | --- | --- |
| 1 | 0.3 | 8 |
| 6 | 0.05 | 1 |
| untreated control | — | 30 |

It will be understood that the specification and examples are illustrative but not limitative of the present invention and that other embodiments within the spirit and scope of the invention will suggest themselves to those skilled in the art.

We claim:

1. A method of repelling slugs and snails comprising applying to a plant infested with or to a locus infested with said slugs and snails a repellent amount of at least one benzoyl urea of the formula

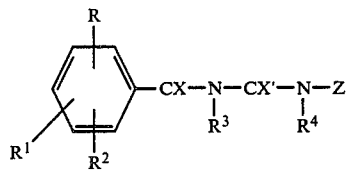

in which
R, $R^1$ and $R^2$ each independently is hydrogen, alkyl or alkoxy of 1 to 6 carbon atoms or halogen,
$R^3$ and $R^4$ each independently is hydrogen, alkyl, alkoxy or alkylthio of 1 to 6 carbon atoms, phenyl, phenoxy, phenylthio, or phenylalkyl, phenylalkoxy or phenylalkylthio having 1 to 4 carbon atoms in the alkyl moiety,
Z is a phenyl, pyridyl, pyridyl-N-oxide, oxazolyl, phenoxyphenyl, pyridyloxyphenyl, phenylazobenzene or phenylpyrimidinyl radical; wherein the radical Z is optionally substituted by at least one of halogen, nitro, cyano, $C_1$-$C_4$-alkyl which can be substituted by fluorine or chlorine, $C_1$-$C_4$-halogenoalkoxy, $C_1$-$C_4$-halogenoalkylthio or —O—$CQ_2$—$CQ_2$—O—, wherein Q each independently is hydrogen, fluorine or chlorine, and
X and X' each independently is oxygen or sulphur.

2. A method according to claim 1, in which the benzoyl urea is of the formula

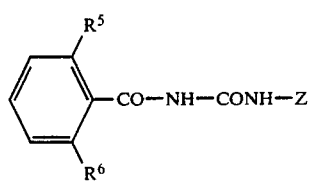

in which
$R^5$ is hydrogen, methyl, methoxy or halogen and,
$R^6$ is methyl, methoxy or halogen.

3. A method according to claim 2, wherein Z is phenyl, phenoxyphenyl or pyridyloxyphenyl.

4. The method according to claim 1, wherein such compound is N-(2-chlorobenzoyl)-$N^1$-(4-trifluoromethoxyphenyl)-urea of the formula

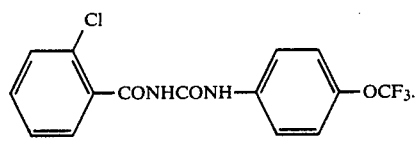

5. The method according to claim 1, wherein such compound is N-(2,6-difluorobenzoyl)-$N^1$-(3,4-(1-chloro-1,2,2-trifluoroethylenedioxy)-phenyl)-urea of the formula

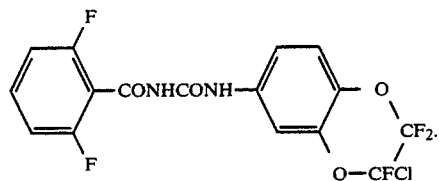

6. The method according to claim 1, wherein such compound is N-(2-chlorobenzoyl)-$N^1$-(4-(2,2-dichloro-1,1-difluoroethoxy)-phenyl)-urea of the formula

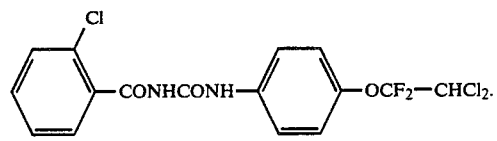

* * * * *

UNITED STATES PATENT AND TRADEMARK OFFICE
CERTIFICATE OF CORRECTION

PATENT NO. : 4,659,736

DATED : April 21, 1987

INVENTOR(S) : Klemens Schlüter, et al.

It is certified that error appears in the above-identified patent and that said Letters Patent is hereby corrected as shown below:

| | |
|---|---|
| Title Page, "Inventors" | Delete "Singapore" second instance |
| Col. 1, line 8 | Delete "board" and substitute --broad-- |
| Col. 2, line 43 | After "aromatic" delete "of" and substitute --or-- |
| Col. 7, line 16 | Delete "De" and substitute --DE-- |
| Col. 7, line 26 | After "4,103,022) delete "pO DE-" |
| Col. 7, line 27 | Before "A" insert --DE-- |
| Col. 8, line 66 | Delete "is" and substitute --it-- |
| Col. 9, line 11 | Delete "are" and substitute --as-- |
| Col. 9, line 28 | Delete "an" and substitute --and-- |
| Col. 12, line 13 | Delete "X'" and substitute --$X^1$-- |

Signed and Sealed this

Twenty-fourth Day of November, 1987

Attest:

DONALD J. QUIGG

Attesting Officer

Commissioner of Patents and Trademarks